(12) United States Patent
Griffith et al.

(10) Patent No.: US 10,662,213 B2
(45) Date of Patent: *May 26, 2020

(54) GEMCITABINE PRODRUGS

(71) Applicant: NuCana plc, Edinburgh (GB)

(72) Inventors: Hugh Griffith, Edinburgh (GB);
Christopher McGuigan, Cardiff South Glamorgan (GB); Magdalena Slusarczyk, Cardiff South Glamorgan (GB); Michaela Serpi, Cardiff South Glamorgan (GB); Valentina Ferrari, Cardiff South Glamorgan (GB)

(73) Assignee: NuCana plc, Edinburgh (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/308,491

(22) PCT Filed: Jun. 25, 2015

(86) PCT No.: PCT/GB2015/051857
§ 371 (c)(1),
(2) Date: Nov. 2, 2016

(87) PCT Pub. No.: WO2015/198058
PCT Pub. Date: Dec. 30, 2015

(65) Prior Publication Data
US 2017/0107246 A1   Apr. 20, 2017

(30) Foreign Application Priority Data

Jun. 25, 2014 (GB) .................................. 1411253.6
Jun. 25, 2014 (IN) .......................... 2050/MUM/2014

(51) Int. Cl.
*A61K 31/7068* (2006.01)
*C07H 19/10* (2006.01)

(52) U.S. Cl.
CPC ......... *C07H 19/10* (2013.01); *A61K 31/7068* (2013.01)

(58) Field of Classification Search
None
See application file for complete search history.

(56) References Cited

U.S. PATENT DOCUMENTS

| 6,069,252 | A | 5/2000 | Liotta et al. |
| 6,703,396 | B1 | 3/2004 | Liotta et al. |
| 7,608,599 | B2 | 10/2009 | Klumpp et al. |
| 7,951,787 | B2 * | 5/2011 | McGuigan ............. C07H 19/10 514/49 |
| 8,642,756 | B2 | 2/2014 | Ross et al. |
| 8,871,737 | B2 | 10/2014 | Smith et al. |
| 8,933,053 | B2 | 1/2015 | McGuigan et al. |
| 9,834,577 | B2 | 12/2017 | Dammalapati et al. |
| 10,005,810 | B2 * | 6/2018 | McGuigan ............... C07H 1/00 |
| 10,117,888 | B2 * | 11/2018 | Griffith ................ A61K 47/18 |
| 2003/0109697 | A1 | 6/2003 | Shepard et al. |
| 2012/0052046 | A1 | 3/2012 | Chamberlain et al. |
| 2017/0226147 | A1 | 8/2017 | Griffith |
| 2018/0271889 | A1 | 9/2018 | Griffith |
| 2018/0273575 | A1 | 9/2018 | McGuigan et al. |
| 2018/0289733 | A1 | 10/2018 | Griffith et al. |
| 2018/0362571 | A1 | 12/2018 | Kotala et al. |
| 2019/0022117 | A1 | 1/2019 | Griffith |
| 2019/0022118 | A1 | 1/2019 | Griffith et al. |

FOREIGN PATENT DOCUMENTS

| WO | WO-9937753 A1 | 7/1999 |
| WO | WO-2001/007454 A1 | 2/2001 |
| WO | WO-2005012327 A2 | 2/2005 |
| WO | WO-2006/081363 A2 | 8/2006 |
| WO | WO-2007/092620 A2 | 8/2007 |
| WO | WO-2010/063701 A2 | 6/2010 |
| WO | WO-2011/062503 A1 | 5/2011 |
| WO | WO-2013/107515 A1 | 7/2013 |
| WO | WO-2014076490 A1 | 5/2014 |
| WO | WO-2015/038596 A1 | 3/2015 |
| WO | WO-2015081133 A2 | 6/2015 |
| WO | WO-2015/198058 A1 | 12/2015 |
| WO | WO-2015/198059 A1 | 12/2015 |
| WO | WO-2016/012781 A1 | 1/2016 |
| WO | WO-2016/055769 A1 | 4/2016 |
| WO | WO-2016/181093 A1 | 11/2016 |
| WO | WO-2017/060661 A1 | 4/2017 |
| WO | WO-2017/098252 A1 | 6/2017 |
| WO | WO-2017/109444 A1 | 6/2017 |

(Continued)

OTHER PUBLICATIONS

Slusarczyk et al., Journal of Medicinal Chemistry, Feb. 2014, vol. 57, No. 4, pp. 1531-1542.*
Slusarczyk, M. et al., "Application of ProTide Technology to Gemcitabine: A Successful Approach to Overcome the Key Cancer Resistance Mechanisms Leads to a New Agent (NUC-1031) in Clinical Development," Journal of Medicinal Chemistry, vol. 57, No. 4, p. 1531-1542, Feb. 27, 2014.
International Search Report dated Aug. 6, 2015 from corresponding Application No. PCT/GB2015/051857.

(Continued)

*Primary Examiner* — Traviss C McIntosh, III
(74) *Attorney, Agent, or Firm* — Dana M. Gordon; Foley Hoag LLP (57) ABSTRACT

This invention relates to a prodrug of the monophosphate nucleotide of the well-known oncology drug gemcitabine. Specifically, it relates to gemcitabine-[phenyl-benzoxy-L-alaninyl)]-phosphate when present as a single phosphate diastereoisomer and, in particular, it relates to the (S)-phosphate diastereoisomer which offers a remarkable and unexpected increase in solubility relative to the (R)-diastereoisomer. The (S)-phosphate epimer is also preferentially taken up into cyclodextrin solutions over the (R)-diastereoisomer.

13 Claims, 4 Drawing Sheets

(56) References Cited

FOREIGN PATENT DOCUMENTS

| WO | WO-2017/109485 A1 | 6/2017 |
| WO | WO-2017/109486 A1 | 6/2017 |

OTHER PUBLICATIONS

U.S. Appl. No. 16/065,369, Griffith et al.
U.S. Appl. No. 16/065,476, Griffith et al.
Harris et al., "Synthesis and antiviral evaluation of phosphoramidate derivatives of (E)-5-(2-bromovinyl)-2'-deoxyuridine," Antiviral Chem Chemother 12:293-300 (2001).
Lackey et al., "Enxyme-catalyzed therapeutic agent (ECTA) design: activation of the antitumor ECTA compound NB1011 by thymidylate synthase," Biochem Pharmacol 61:179-189 (2001).
McGuigan et al., "Phosphoramidate derivatives of AZT as inhibitors of HIV:studies on the carboxyl terminus," Antiviral Chem Chemother 4(2):97-101 (1993).
McGuigan et al., "Synthesis and Evaluation of some masked phosphate esters of the anti-herpesvirus drug 882C (Netivudine) as potential antiviral agents," Antiviral Chem Chemother 9:233-243 (1998).
McGuigan, "A phosphoramidate ProTide (NUC-1031) and acquired and intrinsic resistance to gemcitabine," J Clin Oncol, 29:E13540 (2011).
McIntee et al., "Amino Acid Phosphoramidate Nucleosides: Potential ADEPT/GDEPT Substrates," Bioorg Med Chem Letts 11:2803-2805 (2001).
Siddiqui, "Design and Synthesis of Lipophilic Phosphoramidate d4T-MP Prodrugs Expressing High Potency Against HIV in Cell Culture: Structural Determinants for in Vitro Activity and QSAR," J Med Chem 42:4211-4128 (1999).
Wu, et al., "Synthesis and Biological Activity of Gemcitabine Phosphoramidate Prodrug," J Med Chem, 50(15): 3743-3746 (2007).
U.S. Appl. No. 15/279,611, McGuigan.
International Search Report and Written Opinion for International Application No. PCT/GB2004/003148 dated Jan. 20, 2005.
Bilir et al., "Acetaminophen and DMSO modulate growth and gemcitabine cytotoxicity in FM3A breast cancer cells in vitro," Neoplasma 51(6):460-464 (2004).
Uekama, "Novel Approach of Cyclodextrin-based Pharmaceutical Formulation," Yakugaku Zasshi, 132(1):85-105 (2012).

* cited by examiner

GEMCITABINE PRODRUGS

RELATED APPLICATIONS

This application is a § 371 national stage application based on Patent Cooperation Treaty Application serial number PCT/GB2015/051857, filed Jun. 25, 2015; which claims the benefit of priority to GB 1411253.6, filed Jun. 25, 2014; and IN 2050/MUM/2014, filed Jun. 25, 2014.

This invention relates to a prodrug of the monophosphate of the well-known oncology drug gemcitabine. Specifically, it relates to gemcitabine-[phenyl-benzoxy-L-alaninyl)]-phosphate (chemical name: 2'-Deoxy-2',2'-difluoro-D-cytidine-5'-O-[phenyl (benzoxy-L-alaninyl)] phosphate) when present as a single phosphate diastereoisomer and, in particular, it relates to the (S)-phosphate diastereoisomer which offers a remarkable and unexpected increase in solubility relative to the (R)-diastereoisomer. The (S)-phosphate diastereoisomer is also preferentially taken up into cyclodextrin solutions over the (R)-diastereoisomer.

BACKGROUND

Gemcitabine (1; marketed as Gemzar®) is an effective nucleoside analogue that is currently approved to treat breast, non-small cell lung, ovarian and pancreatic cancers and widely used to treat a variety of other cancers including bladder, biliary, colorectal and lymphoma.

1

Gemcitabine's clinical utility is limited by a number of inherent and acquired resistance mechanisms. At the cellular level resistance is dependent on three parameters: (i) the down-regulation of deoxycytidine kinase, necessary for the activation into the phosphorylated moiety; (ii) the reduced expression of nucleoside transporters, in particular, hENT1 required for uptake by cancer cells; and (iii) the up-regulation of catalytic enzymes especially cytidine deaminase that degrades gemcitabine.

WO2005/012327 describes a series of nucleotide prodrugs for gemcitabine and related nucleoside drug molecules. Among them gemcitabine-[phenyl-benzoxy-L-alaninyl)]-phosphate (NUC-1031; 2) is identified as a particularly effective compound.

These prodrugs appear to avoid many of the inherent and acquired resistance mechanisms which limit the utility of gemcitabine (*Application of ProTide Technology to Gemcitabine: A Successful Approach to Overcome the Key Cancer Resistance Mechanisms Leads to a New Agent* (NUC-1031) in Clinical Development'; Slusarczyk et all; *J. Med. Chem.*; 2014, 57, 1531-1542).

NUC-1031 2 is prepared as a mixture of two diastereoisomers, epimeric at the phosphate centre.

2

Unfortunately, NUC-1031 2 is extremely lipophillic and thus poorly water soluble (by calculation: <0.1 mg/mL), and the ionisable moieties, pyrimidine nitrogen and phenolic hydroxyl have calculated pKas that lie out-side the pH range suitable for parenteral administration. It is essentially insoluble in water, regardless of salt content or pH, and this has implications for the development of formulations for delivering the prodrug at sufficiently high dosages for effective treatment. It also has implications for the development of efficient manufacturing processes which will allow NUC-1031 to be produced cost effectively.

It is an aim of certain embodiments of this invention to provide gemcitabine-[phenyl-benzoxy-L-alaninyl)]-phosphate (NUC-1031; 2) in a form which can be formulated into a effective pharmaceutical composition.

It is also an aim of certain embodiments of this invention to provide a form of gemcitabine-[phenyl-benzoxy-L-alaninyl)]-phosphate (NUC-1031; 2) which can be prepared and stored for an extended period of time.

It is an aim of certain embodiments of this invention to provide gemcitabine-[phenyl-benzoxy-L-alaninyl)]-phosphate (NUC-1031; 2) in a form which has a higher solubility than prior art forms.

It is an aim of certain embodiments of this invention to provide gemcitabine-[phenyl-benzoxy-L-alaninyl)]-phosphate (NUC-1031; 2) as a single diastereoisomer at phosphorus.

Certain embodiments of this invention satisfy some or all of the above aims.

The gemcitabine-[phenyl-benzoxy-L-alaninyl)]-phosphate of the current invention is preferably of substantially the same activity as gemcitabine-[phenyl-benzoxy-L-alaninyl)]-phosphate (NUC-1031; 2). It may, however, have slightly lower activity but have other benefits as described in this specification if there is a manufacturing or therapeutic benefit to the use of it in this form.

BRIEF SUMMARY OF THE DISCLOSURE

In accordance with the present invention there is provided gemcitabine-[phenyl-benzoxy-L-alaninyl)]-(S)-phosphate 3:

or a pharmaceutically acceptable salt or solvate thereof. Preferably, the gemcitabine-[phenyl-benzoxy-L-alaninyl)]-(S)-phosphate 3 is in a substantially diastereoisomerically pure form.

The inventors have discovered a surprising and remarkable difference in the solubilities of the two diastereoisomers. The (S)-epimer 3 has sufficient solubility in mixtures of a number of polar organic solvents with water to render it suitable for formulation and administration as a therapeutic agent. The (R)-epimer 4 is substantially insoluble in most of the solvent mixtures measured. This remarkable difference in solubility had not previously been identified and the potential benefits of this property of the (S)-epimer had not been identified. In a number of the solvent mixtures tested the difference in solubility between the (S)-epimer and the (R)-epimer is over 100 fold.

Surprisingly, the (S)-epimer is also preferentially taken up into cyclodextrin solutions over the (R)-epimer. This has not been observed with other gemcitabine phosphate derivatives.

In a second aspect of the present invention is provided a pharmaceutical formulation comprising gemcitabine-[phenyl-benzoxy-L-alaninyl)]-(S)-phosphate 3, or a pharmaceutically acceptable salt or solvate thereof, having a diastereoisomeric purity of greater than about 90%, and at least one pharmaceutically acceptable excipient.

The formulation may be for parenteral, e.g. for intravenous, subcutaneous or intramuscular administration. Preferably, the formulation is for intravenous administration.

The formulation may be an aqueous formulation which optionally also comprises a polar organic solvent. In the case of parenteral (e.g. intravenous) administration, the formulation preferably also comprises a polar organic solvent.

The formulation may also comprise a cyclodextrin.

In a third aspect of the invention is provided gemcitabine-[phenyl-benzoxy-L-alaninyl)]-(S)-phosphate 3, or a pharmaceutically acceptable salt or solvate thereof, for medical use.

In a fourth aspect of the invention is provided gemcitabine-[phenyl-benzoxy-L-alaninyl)]-(S)-phosphate 3, or a pharmaceutically acceptable salt or solvate thereof, for use in treating cancer.

In a fifth aspect of the invention is provided gemcitabine-[phenyl-benzoxy-L-alaninyl)]-(S)-phosphate 3, or a pharmaceutically acceptable salt or solvate thereof, for use in the manufacture of a medicament for treating cancer.

In a sixth aspect of the invention is provided a method of treating cancer, the method comprising administering to a subject in need thereof a therapeutically effective amount of gemcitabine-[phenyl-benzoxy-L-alaninyl)]-(S)-phosphate 3, or a pharmaceutically acceptable salt or solvate thereof.

A solvate will typically be a hydrate. Thus, the gemcitabine-[phenyl-benzoxy-L-alaninyl)]-(S)-phosphate may be in the form of a salt or hydrate. It may be that the gemcitabine-[phenyl-benzoxy-L-alaninyl)]-(S)-phosphate is not in the form of a salt and/or a solvate (e.g. hydrate). Preferably, it is in the form of the free base.

The gemcitabine-[phenyl-benzoxy-L-alaninyl)]-(S)-phosphate may have a diastereoisomeric purity of greater than about 90%. It may have a diastereoisomeric purity of greater than 95%, 98%, 99%, or even 99.5%. 'Substantially diastereomerically pure' is defined for the purposes of this invention as a diastereomeric purity of greater than about 90%.

The cancer may be a cancer selected from: pancreatic cancer, breast cancer, ovarian cancer, bladder cancer, colorectal cancer, lung cancer, bladder cancer, prostate cancer, cholangiocarcinoma, renal cancer, cervical cancer, thymic cancer, a cancer of an unknown primary origin. The cancer may also be lymphoma or leukemia.

In a seventh aspect of the invention is provided a method of providing at least one diastereoisomer of gemcitabine-[phenyl-benzoxy-L-alaninyl)]-phosphate in a substantially diastereoisomerically pure form, the method comprising the steps of:

obtaining a mixture of gemcitabine-[phenyl-benzoxy-L-alaninyl)]-(R)-phosphate 4 and gemcitabine-[phenyl-benzoxy-L-alaninyl)]-(S)-phosphate 3;

subjecting the mixture to a separation technique; and once separated, isolating gemcitabine-[phenyl-benzoxy-L-alaninyl)]-(R)-phosphate 4 and/or gemcitabine-[phenyl-benzoxy-L-alaninyl)]-(S)-phosphate 3 in a substantially diastereoisomerically pure form.

In a eighth aspect of the invention is provided a method of providing at least one diastereoisomer of gemcitabine-[phenyl-benzoxy-L-alaninyl)]-phosphate in a substantially diastereoisomerically pure form, the method comprising the steps of:

obtaining a mixture of 3'-protected gemcitabine-[phenyl-benzoxy-L-alaninyl)]-(R)-phosphate 4 and 3'-protected gemcitabine-[phenyl-benzoxy-L-alaninyl)]-(S)-phosphate 3;

subjecting the mixture to a separation technique;

once separated, isolating 3'-protected gemcitabine-[phenyl-benzoxy-L-alaninyl)]-(R)-phosphate 4 and/or 3'-protected gemcitabine-[phenyl-benzoxy-L-alaninyl)]-(S)-phosphate 3 in a substantially diastereoisomerically pure form;

removing the 3'-protecting group from one or both of the separated diastereoisomers to provide gemcitabine-[phenyl-benzoxy-L-alaninyl)]-(R)-phosphate 4 and/or gemcitabine-[phenyl-benzoxy-L-alaninyl)]-(S)-phosphate 3 in a substantially diastereoisomerically pure form.

A 3'-protected gemcitabine-[phenyl-benzoxy-L-alaninyl)]-phosphate is a derivative of gemcitabine-[phenyl-benzoxy-L-alaninyl)]-phosphate in which the 3'-hydroxy group features a hydroxyl protecting group. The protecting group in question must be removable cleanly. Exemplary protecting groups include silyl protecting groups (e.g. tert-butyldimethylsilyl and triethylsilyl) in which case the protecting group may be removed using a reagent selected from TFA, HF, fluorosilicic acid and tetrabutylammonium fluoride. An alternative protecting group would be a carbonate group (e.g. tertbutylcarbonate) in which case the protecting group may be removed using a Bronsted acid (e.g. TFA) or a Lewis acid (e.g. $ZnBr_2$).

The separation technique may be chromatography, e.g. column chromatography, preparative thin layer chromatography or preparative HPLC. Where the separation technique is preparative HPLC, it may be carried out using a chiral column, e.g. one comprising amylose tris (3,5-dimethylphenylcarbamate). An example of a chiral column useful in the process of the invention is Chiralpak AD™; the stationary phase of which consists of a 20 µm silica support onto which amylose tris (3,5-dimethylphenylcarbamate) has been physically coated.

The separation technique may be selective uptake into a cyclodextrin solution. This technique involves contacting the mixture with a cyclodextrin solution such that one epimer is taken up into the cyclodextrin solution in preference to the other epimer, and then separating the cyclodextrin solution from the undissolved solid. The cyclodextrin solution may be an aqueous cyclodextrin solution. The separation of the solution from the solid may be achieved by filtration.

The invention also provides gemcitabine-[phenyl-benzoxy-L-alaninyl)]-(R)-phosphate 4:

or a pharmaceutically acceptable salt or solvate thereof. The invention also provides a pharmaceutical formulation comprising gemcitabine-[phenyl-benzoxy-L-alaninyl)]-(R)-phosphate 4, or a pharmaceutically acceptable salt or solvate thereof, having a diastereoisomeric purity of greater than about 90%, and a pharmaceutically acceptable excipient, as well as medical uses of compound 4 and methods of treatment using compound 4. These aspects of the (R)-epimer correspond to those described in relation to compound 3 in the third to sixth aspects of the invention described above. The gemcitabine-[phenyl-benzoxy-L-alaninyl)]-(R)-phosphate may be in a substantially diastereoisomerically pure form. It may be that the gemcitabine-[phenyl-benzoxy-L-alaninyl)]-(R)-phosphate is not a salt and/or a solvate (e.g. hydrate). Preferably, it is present as the free base.

The R-epimer has been shown to have a half-life on incubation with isolated human hepatic cells which is four times that of the S-epimer (see Example 4). The longer half-life associated with R-isomer indicates a lower intrinsic clearance and should result in a different pharmacokinetic and pharmacodynamic profile to the S-isomer. This profile may mean a higher and more prolonged concentration of the R-isomer in the systemic circulation and hence greater exposure to the R-epimer than would be achieved with the S-epimer. The AUC for the R-isomer could therefore be higher, resulting in greater and more prolonged exposure to the moiety, for example, for oral route of administration where first pass effects are more pronounced. This prolonged exposure to the R-epimer could allow for substantially prolonged tumour exposure to the R-epimer and may result in greater efficacy, where the reduced first pass metabolism in the liver will result in higher drug concentrations. This different property could also allow for targeting of specific tumours where a longer PK profile may result in greater efficacy in hard to access tumour sites where vasculature is poor. Prolonged exposure to the R-epimer may ensure adequate drug concentration of the active metabolite through more phases of the cell cycle, including cell division.

BRIEF DESCRIPTION OF THE DRAWINGS

Embodiments of the invention are further described hereinafter with reference to the accompanying drawings, in which.

DETAILED DESCRIPTION

Throughout this specification, the term S-epimer or S-diastereoisomer refers to gemcitabine-[phenyl-benzoxy-L-alaninyl)]-(S)-phosphate. Likewise, throughout this specification, the term R-epimer or R-diastereoisomer refers to gemcitabine-[phenyl-benzoxy-L-alaninyl)]-(R)-phosphate.

The compounds of the present invention can be used in the treatment of the human body. They may be used in the treatment of the animal body. In particular, the compounds of the present invention can be used to treat commercial animals such as livestock. Alternatively, the compounds of the present invention can be used to treat companion animals such as cats, dogs, etc.

The compounds of the invention may be obtained, stored and/or administered in the form of a pharmaceutically acceptable salt. Suitable pharmaceutically acceptable salts include, but are not limited to, salts of pharmaceutically acceptable inorganic acids such as hydrochloric, sulphuric, phosphoric, nitric, carbonic, boric, sulfamic, and hydrobromic acids, or salts of pharmaceutically acceptable organic acids such as acetic, propionic, butyric, tartaric, maleic, hydroxymaleic, fumaric, malic, citric, lactic, mucic, gluconic, benzoic, succinic, oxalic, phenylacetic, methanesulphonic, toluenesulphonic, benzenesulphonic, salicylic, sulphanilic, aspartic, glutamic, edetic, stearic, palmitic, oleic, lauric, pantothenic, tannic, ascorbic and valeric acids. Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts. Hemisalts of acids and bases may also be formed, for example, hemisulfate, hemioxalate and hemicalcium salts. In certain embodiments, particularly those that apply to the s-epimer, the compound is in the form of a HCl salt or a hemioxalate salt.

Compounds of the invention may exist in a single crystal form or in a mixture of crystal forms or they may be amorphous. Thus, compounds of the invention intended for pharmaceutical use may be administered as crystalline or amorphous products. They may be obtained, for example, as solid plugs, powders, or films by methods such as precipitation, crystallization, freeze drying, or spray drying, or evaporative drying. Microwave or radio frequency drying may be used for this purpose.

For the above-mentioned compounds of the invention the dosage administered will, of course, vary with the compound employed, the mode of administration, the treatment desired and the disorder indicated. For example, if the compound of the invention is administered parenterally, then the dosage of the compound of the invention may be in the range from 0.1 to 5 g/m$^2$, e.g. from 0.5 to 2 g/m$^2$. The size of the dose for therapeutic purposes of compounds of the invention will naturally vary according to the nature and severity of the conditions, the age and sex of the animal or patient and the route of administration, according to well known principles of medicine.

Dosage levels, dose frequency, and treatment durations of compounds of the invention are expected to differ depending on the formulation and clinical indication, age, and co-morbid medical conditions of the patient.

A compound of the invention, or pharmaceutically acceptable salt thereof, may be used on their own but will generally be administered in the form of a pharmaceutical composition in which the compounds of the invention, or pharmaceutically acceptable salt thereof, is in association with a pharmaceutically acceptable adjuvant, diluent or carrier. Conventional procedures for the selection and preparation of suitable pharmaceutical formulations are described in, for example, "Pharmaceuticals—The Science of Dosage Form Designs", M. E. Aulton, Churchill Livingstone, 1988.

Depending on the mode of administration of the compounds of the invention, the pharmaceutical composition which is used to administer the compounds of the invention will preferably comprise from 0.05 to 99% w (percent by weight) compounds of the invention, more preferably from 0.05 to 80% w compounds of the invention, still more preferably from 0.10 to 70% w compounds of the invention, and even more preferably from 0.10 to 50% w compounds of the invention, all percentages by weight being based on total composition.

For oral administration the compounds of the invention may be admixed with an adjuvant or a carrier, for example, lactose, saccharose, sorbitol, mannitol; a starch, for example, potato starch, corn starch or amylopectin; a cellulose derivative; a binder, for example, gelatine or polyvinylpyrrolidone; and/or a lubricant, for example, magnesium stearate, calcium stearate, polyethylene glycol, a wax, paraffin, and the like, and then compressed into tablets. If coated tablets are required, the cores, prepared as described above, may be coated with a concentrated sugar solution which may contain, for example, gum arabic, gelatine, talcum and titanium dioxide. Alternatively, the tablet may be coated with a suitable polymer dissolved in a readily volatile organic solvent.

For the preparation of soft gelatine capsules, the compounds of the invention may be admixed with, for example, a vegetable oil or polyethylene glycol. Hard gelatine capsules may contain granules of the compound using either the above-mentioned excipients for tablets. Also liquid or semisolid formulations of the compound of the invention may be filled into hard gelatine capsules.

Liquid preparations for oral application may be in the form of syrups or suspensions, for example, solutions containing the compound of the invention, the balance being sugar and a mixture of ethanol, water, glycerol and propylene glycol. Optionally such liquid preparations may contain colouring agents, flavouring agents, sweetening agents (such as saccharine), preservative agents and/or carboxymethylcellulose as a thickening agent or other excipients known to those skilled in art.

For parenteral (e.g. intravenous) administration the compounds of the invention may be administered as a sterile aqueous or oily solution. The compounds of the invention are very lipophillic. Aqueous formulations will typically, therefore, also contain a pharmaceutically acceptable polar organic solvent.

Cyclodextrins have been shown to find wide application in drug delivery (Rasheed et al, *Sci. Pharm.*, 2008, 76, 567-598). Cyclodextrins are a family of cyclic oligosaccharides. They act as a 'molecular cage' which encapsulates drug molecules and alters properties of those drug molecules such as solubility. Cyclodextrins comprise (α-1,4)-linked α-D-glucopyranose units. Cyclodextrins may contains 6, 7 or 8 glucopyranose units (designated α-, β- and γ-cyclodextrins respectively). Cyclodextrins used in pharmaceutical formulations are often β-cyclodextrins. The pendant hydroxyl groups can be alkylated with a $C_1$-$C_6$ substituted or unsubstituted alkyl group. Examples of cyclodextrins are α-cyclodextrin, β-cyclodextrin, γ-cyclodextrin, 2-hydroxypropyl-β-cyclodextrin (HP-β-CD), sulfobutylether β-cyclodextrin sodium salt, partially methylated β-cyclodextrin.

The size of the dose for therapeutic purposes of compounds of the invention will naturally vary according to the nature and severity of the conditions, the age and sex of the animal or patient and the route of administration, according to well known principles of medicine.

Dosage levels, dose frequency, and treatment durations of compounds of the invention are expected to differ depending on the formulation and clinical indication, age, and co-morbid medical conditions of the patient.

The present invention also includes all pharmaceutically acceptable isotopically-labelled forms of compounds 3 or 4 wherein one or more atoms are replaced by atoms having the same atomic number, but an atomic mass or mass number different from the atomic mass or mass number of the predominant isotope usually found in nature.

Examples of isotopes suitable for inclusion in the compounds of the invention include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulphur, such as $^{35}$S.

Certain isotopically-labelled compounds, for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection.

Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Topography (PET) studies for examining substrate receptor occupancy.

Isotopically-labelled compounds can generally be prepared by conventional techniques known to those skilled in the art or by processes analogous to those described using an appropriate isotopically-labelled reagent in place of the non-labelled reagent previously employed.

The method of treatment or the compound for use in the treatment of cancer may involve, in addition to the compound of the invention, conventional surgery or radiotherapy or chemotherapy. Such chemotherapy may include the administration of one or more other active agents.

Where a further active agent is administered as part of a method of treatment of the invention, such combination treatment may be achieved by way of the simultaneous, sequential or separate dosing of the individual components of the treatment. Such combination products employ the compounds of this invention within a therapeutically effective dosage range described hereinbefore and the one or more other pharmaceutically-active agent(s) within its approved dosage range.

Thus, the pharmaceutical formulations of the invention may comprise another active agent.

The one or more other active agents may be one or more of the following categories of anti-tumour agents:

(i) antiproliferative/antineoplastic drugs and combinations thereof, such as alkylating agents (for example cyclophosphamide, nitrogen mustard, bendamustin, melphalan, chlorambucil, busulphan, temozolamide and nitrosoureas); antimetabolites (for example gemcitabine and antifolates such as fluoropyrimidines like 5-fluorouracil and tegafur, raltitrexed, methotrexate, pemetrexed, cytosine arabinoside, and hydroxyurea); antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere and polokinase inhibitors); proteasome inhibitors, for example carfilzomib and bortezomib; interferon therapy; and topoisomerase inhibitors (for example epipodophyllotoxins like etoposide and teniposide, amsacrine, topotecan, mitoxantrone and camptothecin);

(ii) cytostatic agents such as antiestrogens (for example tamoxifen, fulvestrant, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) anti-invasion agents, for example dasatinib and bosutinib (SKI-606), and metalloproteinase inhibitors, inhibitors of urokinase plasminogen activator receptor function or antibodies to Heparanase;

(iv) inhibitors of growth factor function: for example such inhibitors include growth factor antibodies and growth factor receptor antibodies, for example the anti-erbB2 antibody trastuzumab [Herceptin™], the anti-EGFR antibody panitumumab, the anti-erbB1 antibody cetuximab, tyrosine kinase inhibitors, for example inhibitors of the epidermal growth factor family (for example EGFR family tyrosine kinase inhibitors such as gefitinib, erlotinib and 6-acrylamido-N-(3-chloro-4-fluorophenyl)-7-(3-morpholinopropoxy)-quinazolin-4-amine (CI 1033), erbB2 tyrosine kinase inhibitors such as lapatinib); inhibitors of the hepatocyte growth factor family; inhibitors of the insulin growth factor family; modulators of protein regulators of cell apoptosis (for example Bcl-2 inhibitors); inhibitors of the platelet-derived growth factor family such as imatinib and/or nilotinib (AMN107); inhibitors of serine/threonine kinases (for example Ras/Raf signalling inhibitors such as farnesyl transferase inhibitors, for example sorafenib, tipifarnib and lonafarnib), inhibitors of cell signalling through MEK and/or AKT kinases, c-kit inhibitors, abl kinase inhibitors, PI3 kinase inhibitors, Plt3 kinase inhibitors, CSF-1R kinase inhibitors, IGF receptor, kinase inhibitors; aurora kinase inhibitors and cyclin dependent kinase inhibitors such as CDK2 and/or CDK4 inhibitors;

(v) antiangiogenic agents such as those which inhibit the effects of vascular endothelial growth factor, [for example the anti-vascular endothelial cell growth factor antibody bevacizumab (Avastin™); thalidomide; lenalidomide; and for example, a VEGF receptor tyrosine kinase inhibitor such as vandetanib, vatalanib, sunitinib, axitinib and pazopanib;

(vi) gene therapy approaches, including for example approaches to replace aberrant genes such as aberrant p53 or aberrant BRCA1 or BRCA2;

(vii) immunotherapy approaches, including for example antibody therapy such as alemtuzumab, rituximab, ibritumomab tiuxetan (Zevalin®) and ofatumumab; interferons such as interferon α; interleukins such as IL-2 (aldesleukin); interleukin inhibitors for example IRAK4 inhibitors; cancer vaccines including prophylactic and treatment vaccines such as HPV vaccines, for example Gardasil, Cervarix, Oncophage and Sipuleucel-T (Provenge); and toll-like receptor modulators for example TLR-7 or TLR-9 agonists; and (viii) cytotoxic agents for example fludaribine (fludara), cladribine, pentostatin (Nipent™);

(ix) steroids such as corticosteroids, including glucocorticoids and mineralocorticoids, for example aclometasone, aclometasone dipropionate, aldosterone, amcinonide, beclomethasone, beclomethasone dipropionate, betamethasone, betamethasone dipropionate, betamethasone sodium phosphate, betamethasone valerate, budesonide, clobetasone, clobetasone butyrate, clobetasol propionate, cloprednol, cortisone, cortisone acetate, cortivazol, deoxycortone, desonide, desoximetasone, dexamethasone, dexamethasone sodium phosphate, dexamethasone isonicotinate, difluorocortolone, fluclorolone, flumethasone, flunisolide, fluocinolone, fluocinolone acetonide, fluocinonide, fluocortin butyl, fluocortisone, fluocortolone, fluocortolone caproate, fluocortolone pivalate, fluorometholone, fluprednidene, fluprednidene acetate, flurandrenolone, fluticasone, fluticasone propionate, halcinonide, hydrocortisone, hydrocortisone acetate, hydrocortisone butyrate, hydrocortisone aceponate, hydrocortisone buteprate, hydrocortisone valerate, icomethasone, icomethasone enbutate, meprednisone, methylprednisolone, mometasone paramethasone, mometasone furoate monohydrate, prednicarbate, prednisolone, prednisone, tixocortol, tixocortol pivalate, triamcinolone, triamcinolone acetonide, triamcinolone alcohol and their respective pharmaceutically acceptable derivatives. A combination of steroids may be used, for example a combination of two or more steroids mentioned in this paragraph;

(x) targeted therapies, for example PI3Kd inhibitors, for example idelalisib and perifosine; or compounds that inhibit PD-1, PD-L1 and CAR T.

The one or more other active agents may also be antibiotics.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

The following abbreviations are used in this specification:
DMF—N,N-dimethylformamide DMSO—dimethylsulfoxide
IPA—isopropyl alcohol NMP—N-methylpyrroldinone
PEG—polyethylene glycol TBDMS—tert-butyldimethylsilyl
TFA—trifluoroacetic acid

Example 1

Figure 1:
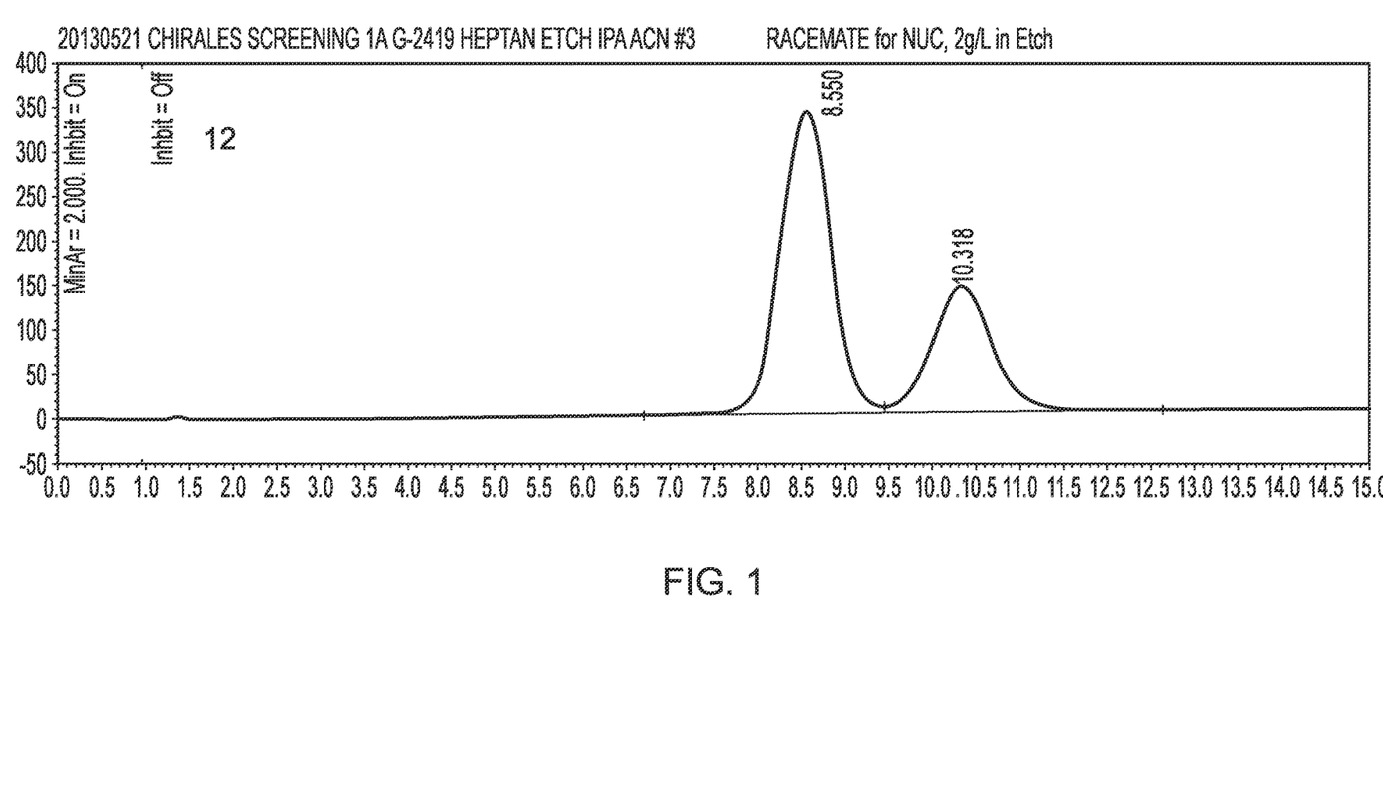
FIG. 1 shows the chromatograph for separation of compounds 3 and 4 by HPLC using a Chiralpak AD column and a n-heptane/IPA gradient solvent system

The (R) and (S) isomers were separated by HPLC under the following conditions:
Equipment: Agilent 1200™ series with DAD detector
Flow rate: 1.0 mL/min
Column: Chiralpak AD™; 250×4.6 mm ID (normal phase)
Temperature: ambient
Particle size: 20 μm
Feed: dissolved in MeOH; 10 g/L
Solvent: n-heptane/IPA 10->50% IPA
The chromatogram is shown in FIG. 1. The (S)-epimer eluted at 8.6 min and the (R)-epimer eluted at 10.3 minutes.

Characterisation Methods and Materials: Proton ($^1$H), carbon ($^{13}$C), phosphorus ($^{31}$P) and fluorine ($^{19}$F) NMR spectra were recorded on a Bruker Avance 500 spectrometer at 25° C. Spectra were auto-calibrated to the deuterated solvent peak and all $^{13}$C NMR and $^{31}$P NMR were proton-decoupled. The purity of final compounds was verified to be >95% by HPLC analysis using Varian Polaris C18-A (10 μM) as an analytic column with a gradient elution of H$_2$O/MeOH from 100/0 to 0/100 in 35 min. The HPLC analysis was conducted by Varian Prostar (LC Workstation-Varian prostar 335 LC detector).

2'-Deoxy-2',2'-difluoro-D-cytidine-5'-O-[phenyl(benzyloxy-L-alaninyl)]-(S)-phosphate 3

(ES+) m/z, found: (M+Na$^+$) 603.14. C$_{25}$H$_{27}$F$_2$N$_4$O$_8$NaP required: (M$^+$) 580.47.
$^{31}$P NMR (202 MHz, MeOD): Op 3.66
$^1$H NMR (500 MHz, MeOD): $\delta_H$ 7.58 (d, J=7.5 Hz, 1H, H-6), 7.38-7.32 (m, 7H, ArH), 7.26-7.20 (m, 3H, ArH), 6.24 (t, J=7.5 Hz, 1H, H-1'), 5.84 (d, J=7.5 Hz, 1H, H-5), 5.20 (AB system, J$_{AB}$=12.0 Hz, 2H, OCH$_2$Ph), 4.46-4.43 (m, 1H, H-5'), 4.36-4.31 (m, 1H, H-5'), 4.25-4.19 (m, 1H, H-3'), 4.07-4.00 (m, 2H, H-4', CHCH$_3$), 1.38 (d, J=7.2 Hz, 3H, CHCH$_3$).
$^{19}$F NMR (470 MHz, MeOD): $\delta_F$ −118.0 (d, J=241 Hz, F), −120.24 (broad d, J=241 Hz, F).
$^{13}$C NMR (125 MHz, MeOD): $\delta_C$ 174.61 (d, $^3$J$_{C-P}$=5.0 Hz, C=O, ester), 167.63 (C—NH$_2$), 157.74 (C=O base), 152.10 (d, $^2$J$_{C-P}$=7.0 Hz, C—Ar), 142.40 (CH-base), 137.22 (C—Ar), 130.90, 129.63, 129.39, 129.32, 126.32 (CH—Ar), 124.51 (d, $^1$J$_{C-F}$=257 Hz, CF$_2$), 121.47, 121.43 (CH—Ar), 96.67 (CH-base), 85.92 (broad signal, C-1'), 80.31 (C-4'), 71.27 (apparent t, $^2$J$_{C-F}$=23.7 Hz, C-3'), 68.03 (OCH$_2$Ph), 65.73 (d, $^2$J$_{C-P}$=5.30 Hz, C-5'), 51.66 (CHCH$_3$), 20.42 (d, $^3$J$_{C-P}$=6.25 Hz, CHCH$_3$).
Reverse HPLC, eluting with H$_2$O/MeOH from 100/0 to 0/100 in 35 min, showed one peak of diastereoisomer with t$_R$=22.53 min.

2'-deoxy-2',2'-difluoro-D-cytidine-5'-O-[phenyl(benzyloxy-L-alaninyl)]-(R)-phosphate 4

Figure 2:
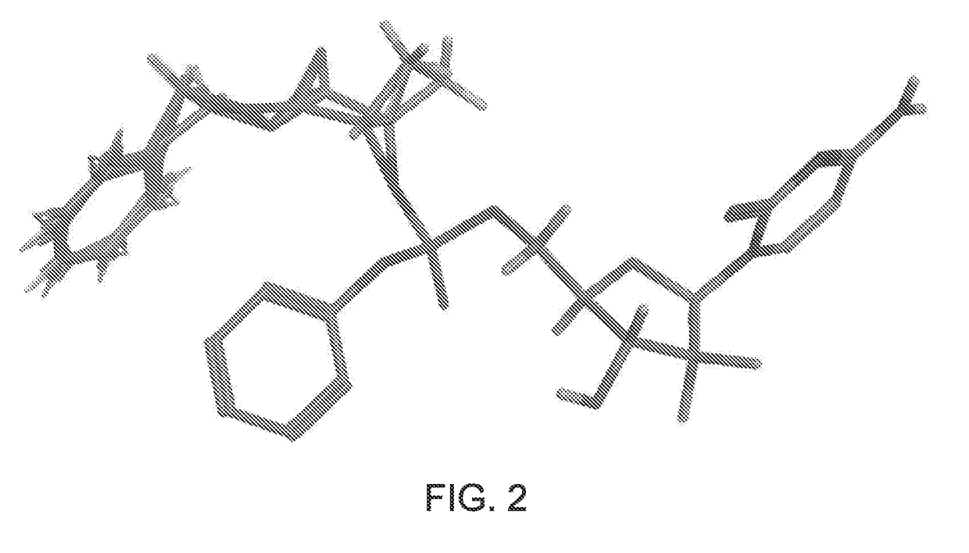
FIG. 2 shows the structure of compound 4 as determined by x-ray diffraction
Figure 3:
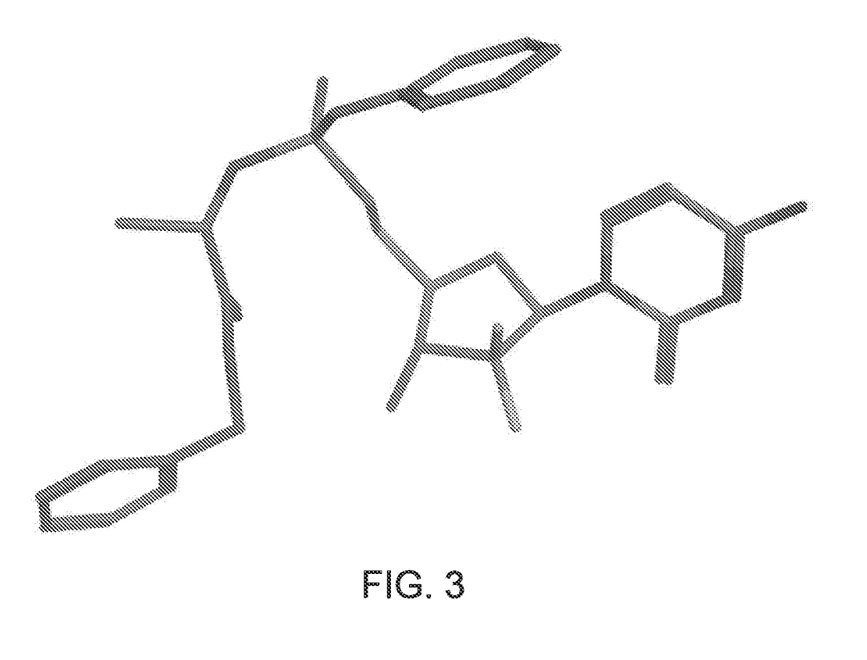
FIG. 3 shows the structure of compound 3 as determined by x-ray diffraction

(ES+) m/z, found: (M+Na$^+$) 603.14. C$_{25}$H$_{27}$F$_2$N$_4$O$_8$NaP required: (M$^+$) 580.47.
$^{31}$P NMR (202 MHz, MeOD): $\delta_P$ 3.83
$^1$H NMR (500 MHz, MeOD): $\delta_H$ 7.56 (d, J=7.5 Hz, 1H, H-6), 7.38-7.31 (m, 7H, ArH), 7.23-7.19 (m, 3H, ArH), 6.26 (t, J=7.5 Hz, 1H, H-1'), 5.88 (d, J=7.5 Hz, 1H, H-5), 5.20 (s, 2H, OCH$_2$Ph), 4.49-4.46 (m, 1H, H-5'), 4.38-4.34 (m, 1H, H-5'), 4.23-4.17 (m, 1H, H-3'), 4.07-4.01 (m, 2H, H-4', CHCH$_3$), 1.38 (d, J=7.2 Hz, 3H, CHCH$_3$).
$^{19}$F NMR (470 MHz, MeOD): $\delta_F$ −118.3 (d, J=241 Hz, F), −120.38 (broad d, J=241 Hz, F).
$^{13}$C NMR (125 MHz, MeOD): $\delta_C$ 174.65 (d, $^3$J$_{C-P}$=5.0 Hz, C=O, ester), 167.65 (C—NH$_2$), 157.75 (C=O base), 152.10 (d, $^2$J$_{C-P}$=7.0 Hz, C—Ar), 142.28 (CH-base), 137.50 (C—Ar), 130.86, 129.63, 129.40, 129.32, 126.31 (CH—Ar), 124.50 (d, $^1$J$_{C-F}$=257 Hz, CF$_2$), 121.44, 121.40 (CH—Ar), 96.67 (CH-base), 85.90 (broad signal, C-1'), 80.27 (C-4'), 71.30 (apparent t, $^2$J$_{C-F}$=23.7 Hz, C-3'), 68.02 (OCH$_2$Ph), 65.50 (C-5'), 51.83 (CHCH$_3$), 20.22 (d, $^3$J$_{C-P}$=7.5 Hz, CHCH$_3$).
Reverse HPLC, eluting with H$_2$O/MeOH from 100/0 to 0/100 in 35 min, showed one peak of diastereoisomer with t$_R$=21.87 min X-ray diffraction data was also obtained for the two isomers and the resulting images are shown in FIGS. 2 and 3. The corresponding diffraction data and methodology is provided in Tables 1 to 4 below.

TABLE 1

Crystal data and structure refinement for (R)-epimer 4.

| | |
|---|---|
| Identification code | shelx |
| Empirical formula | C$_{25}$H$_{27}$F$_2$N$_4$O$_8$P |
| Formula weight | 580.47 |
| Temperature | 296(2) K |
| Wavelength | 1.54184 Å |
| Crystal system | Monoclinic |
| Space group C 2 | |
| Unit cell dimensions | a = 19.2280(3) Å    α = 90°. |
| | b = 10.22330(10) Å  β = 97.966(2)°. |
| | c = 13.6911(2) Å    γ = 90°. |
| Volume | 2665.34(6) Å$^3$ |
| Z | 4 |
| Density (calculated) | 1.447 Mg/m$^3$ |
| Absorption coefficient | 1.541 mm$^{-1}$ |
| F(000) | 1208 |
| Crystal size | 0.584 × 0.095 × 0.051 mm$^3$ |
| Theta range for data collection | 3.259 to 73.477°. |

TABLE 1-continued

Crystal data and structure refinement for (R)-epimer 4.

| | |
|---|---|
| Index ranges | $-23 \leq h \leq 23$, $-12 \leq k \leq 12$, $-17 \leq l \leq 13$ |
| Reflections collected | 9684 |
| Independent reflections | 5150 [R(int) = 0.0239] |
| Completeness to theta = 67.684° | 99.9% |
| Absorption correction | Semi-empirical from equivalents |
| Max. and min. transmission | 1.00000 and 0.61719 |
| Refinement method | Full-matrix least-squares on $F^2$ |
| Data/restraints/parameters | 5150/549/437 |
| Goodness-of-fit on $F^2$ | 1.065 |
| Final R indices [I > 2sigma(I)] | R1 = 0.0646, wR2 = 0.1759 |
| R indices (all data) | R1 = 0.0681, wR2 = 0.1793 |
| Absolute structure parameter | 0.039(10) |
| Extinction coefficient | n/a |
| Largest diff. peak and hole | 0.477 and −0.917 e · Å$^{-3}$ |

TABLE 2

Atomic coordinates (×10$^4$) and equivalent isotropic displacement parameters (Å$^2$ × 10$^3$) for (R)-epimer 4. U(eq) is defined as one third of the trace of the orthogonalized U$^{ij}$ tensor.

| | x | y | z | U(eq) |
|---|---|---|---|---|
| N(1) | 746(2) | 9565(4) | 4120(3) | 35(1) |
| C(1) | 1373(2) | 10267(5) | 4426(4) | 40(1) |
| C(2) | 779(3) | 12200(5) | 4030(4) | 40(1) |
| C(3) | 131(3) | 11526(5) | 3717(4) | 45(1) |
| C(4) | 141(3) | 10216(5) | 3785(4) | 39(1) |
| C(5) | 723(2) | 8163(4) | 4257(4) | 33(1) |
| C(6) | 1301(2) | 6686(5) | 5412(3) | 34(1) |
| C(7) | 1730(2) | 6675(4) | 4553(3) | 33(1) |
| C(8) | 1228(3) | 7319(5) | 3735(4) | 37(1) |
| C(9) | 1755(3) | 6761(6) | 6387(4) | 43(1) |
| C(10) | 1727(3) | 3180(6) | 7861(5) | 50(1) |
| C(11) | 1763(4) | 2447(7) | 7027(5) | 61(2) |
| C(12) | 1751(4) | 1097(8) | 7088(7) | 75(2) |
| C(13) | 1724(5) | 533(8) | 7970(9) | 94(3) |
| C(14) | 1685(6) | 1247(9) | 8799(8) | 97(3) |
| C(15) | 1693(5) | 2625(8) | 8758(6) | 78(2) |
| P(1) | 1047(1) | 5375(1) | 7561(1) | 43(1) |
| F(1) | 1535(2) | 7981(3) | 3064(2) | 54(1) |
| F(2) | 828(2) | 6372(3) | 3227(2) | 54(1) |
| N(2) | 792(3) | 13496(4) | 3968(4) | 53(1) |
| N(3) | 1370(2) | 11570(4) | 4362(4) | 44(1) |
| O(1) | 1897(2) | 9608(4) | 4734(4) | 54(1) |
| O(2) | 868(2) | 7849(4) | 5276(3) | 42(1) |
| O(3) | 1921(2) | 5414(4) | 4294(3) | 42(1) |
| O(4) | 1354(2) | 6700(4) | 7211(3) | 48(1) |
| O(5) | 1755(2) | 4556(4) | 7796(3) | 51(1) |
| O(6) | 514(2) | 4743(5) | 6869(4) | 63(1) |
| N(4) | 789(3) | 5715(6) | 8600(5) | 69(1) |
| O(7) | 595(4) | 5712(9) | 10681(7) | 76(1) |
| O(8) | 1614(5) | 4778(9) | 10851(7) | 73(1) |
| C(16) | 1339(8) | 6191(13) | 9486(10) | 72(1) |
| C(17) | 1345(8) | 7650(14) | 9611(10) | 75(1) |
| C(18) | 1162(8) | 5543(19) | 10418(11) | 73(1) |
| C(19) | 1420(3) | 4227(5) | 11796(4) | 74(1) |
| C(20) | 1213(3) | 2833(5) | 11556(4) | 74(1) |
| C(21) | 1737(3) | 1889(5) | 11701(4) | 74(1) |
| C(22) | 1562(3) | 570(5) | 11626(4) | 74(1) |
| C(23) | 863(3) | 195(5) | 11406(4) | 73(1) |
| C(24) | 339(3) | 1139(5) | 11261(4) | 74(1) |
| C(25) | 514(3) | 2458(5) | 11336(4) | 74(1) |
| N(4A) | 789(3) | 5715(6) | 8600(5) | 69(1) |
| O(7A) | 643(8) | 6651(15) | 10878(10) | 71(1) |
| O(8A) | 1156(10) | 4892(18) | 10491(12) | 73(1) |
| C(16A) | 1034(13) | 6570(20) | 9296(16) | 72(1) |
| C(17A) | 797(12) | 7900(20) | 9187(16) | 74(2) |
| C(18A) | 945(13) | 6100(20) | 10317(17) | 72(1) |
| C(19A) | 974(5) | 4324(9) | 11444(7) | 74(1) |
| C(20A) | 986(5) | 2873(9) | 11442(7) | 74(1) |
| C(21A) | 1654(5) | 2345(9) | 11684(7) | 74(1) |
| C(22A) | 1747(5) | 996(9) | 11687(7) | 74(1) |
| C(23A) | 1172(5) | 176(9) | 11448(7) | 74(1) |
| C(24A) | 504(5) | 704(9) | 11206(7) | 74(1) |
| C(25A) | 411(5) | 2052(9) | 11203(7) | 74(1) |

TABLE 3

Crystal data and structure refinement for (S)-epimer 3.

| | |
|---|---|
| Identification code | shelx |
| Empirical formula | $C_{25.29}H_{26.44}F_2N_{4.14}O_8P$ |
| Formula weight | 585.44 |
| Temperature | 293(2) K |
| Wavelength | 1.54184 Å |
| Crystal system | Monoclinic |
| Space group | P 2$_1$ |
| Unit cell dimensions | a = 11.3844(3) Å  α = 90°. |
| | b = 34.8283(7) Å  β = 111.282(4)°. |
| | c = 15.1260(6) Å  γ = 90°. |
| Volume | 5588.5(3) Å3 |
| Z | 8 |
| Density (calculated) | 1.392 Mg/m3 |
| Absorption coefficient | 1.477 mm−1 |
| F(000) | 2434 |
| Crystal size | 0.249 × 0.072 × 0.042 mm3 |
| Theta range for data collection | 3.135 to 73.481°. |
| Index ranges | $-13 \leq h \leq 12$, $-42 \leq k \leq 42$, $-17 \leq l \leq 18$ |
| Reflections collected | 43816 |
| Independent reflections | 21792 [R(int) = 0.0582] |
| Completeness to theta = 67.684° | 100.0% |
| Absorption correction | Semi-empirical from equivalents |
| Max. and min. transmission | 1.00000 and 0.62509 |
| Refinement method | Full-matrix least-squares on F2 |
| Data/restraints/parameters | 21792/2/1478 |
| Goodness-of-fit on F2 | 1.022 |
| Final R indices [I > 2sigma(I)] | R1 = 0.0628, wR2 = 0.1597 |
| R indices (all data) | R1 = 0.0921, wR2 = 0.1794 |
| Absolute structure parameter | 0.031(13) |
| Extinction coefficient | n/a |
| Largest diff. peak and hole | 0.513 and −0.413 e · Å−3 |

TABLE 4

Atomic coordinates (×104) and equivalent isotropic displacement parameters (Å2 × 103) for the (S)-epimer 3. U(eq) is defined as one third of the trace of the orthogonalized Uij tensor.

| | x | y | z | U(eq) |
|---|---|---|---|---|
| C(1) | −2481(7) | 1599(2) | 6585(6) | 35(2) |
| C(2) | −4079(6) | 1825(2) | 7037(5) | 36(2) |
| C(3) | −3292(7) | 2138(2) | 7558(6) | 40(2) |
| C(4) | −2138(7) | 2159(2) | 7573(6) | 40(2) |
| C(5) | −417(6) | 1916(2) | 7113(6) | 37(2) |
| C(6) | 1520(6) | 2176(2) | 7885(6) | 37(2) |
| C(7) | 1182(7) | 2311(2) | 6853(6) | 41(2) |
| C(8) | −198(7) | 2183(2) | 6399(6) | 42(2) |
| C(9) | 2187(7) | 2464(2) | 8638(6) | 40(2) |
| C(10) | −428(7) | 3331(2) | 8699(6) | 42(2) |
| C(11) | −661(8) | 3061(2) | 9279(7) | 52(2) |
| C(12) | −1894(8) | 2980(2) | 9149(8) | 53(2) |
| C(13) | −2880(8) | 3159(3) | 8495(7) | 59(2) |
| C(14) | −2631(9) | 3426(3) | 7913(9) | 71(3) |
| C(15) | −1403(9) | 3517(3) | 8012(7) | 61(2) |
| C(16) | 3026(7) | 3528(2) | 8008(6) | 44(2) |
| C(17) | 4074(8) | 3825(2) | 8156(7) | 52(2) |
| C(18) | 3226(7) | 3213(2) | 7405(6) | 46(2) |

TABLE 4-continued

Atomic coordinates (×104) and equivalent isotropic displacement parameters (Å2 × 103) for the (S)-epimer 3. U(eq) is defined as one third of the trace of the orthogonalized Uij tensor.

| | x | y | z | U(eq) |
|---|---|---|---|---|
| C(19) | 2875(10) | 3054(3) | 5787(8) | 65(3) |
| C(20) | 4128(8) | 3142(2) | 5690(6) | 46(2) |
| C(21) | 4412(9) | 3504(2) | 5462(6) | 48(2) |
| C(22) | 5504(9) | 3580(3) | 5340(7) | 59(2) |
| C(23) | 6360(9) | 3281(3) | 5425(8) | 67(3) |
| C(24) | 6068(10) | 2917(3) | 5643(9) | 73(3) |
| C(25) | 4979(10) | 2851(3) | 5777(7) | 62(2) |
| N(1) | −1680(6) | 1893(2) | 7097(5) | 36(1) |
| N(2) | −3652(6) | 1572(2) | 6561(5) | 38(1) |
| N(3) | −5247(6) | 1787(2) | 7003(6) | 50(2) |
| N(4) | 3092(6) | 3390(2) | 8954(5) | 44(2) |
| O(1) | −2035(5) | 1369(2) | 6152(5) | 49(1) |
| O(2) | 360(5) | 2074(1) | 7991(4) | 39(1) |
| O(3) | 1997(5) | 2165(2) | 6434(5) | 50(2) |
| O(4) | 1475(5) | 2819(1) | 8445(4) | 39(1) |
| O(5) | 805(5) | 3441(1) | 8776(4) | 41(1) |
| O(6) | 2374(5) | 3056(2) | 10168(4) | 43(1) |
| O(7) | 3851(5) | 2925(2) | 7682(5) | 51(1) |
| O(8) | 2644(6) | 3304(2) | 6471(5) | 57(2) |
| P(1) | 1979(2) | 3167(1) | 9166(1) | 38(1) |
| F(1) | −960(4) | 2496(2) | 6274(4) | 56(1) |
| F(2) | −474(5) | 2023(2) | 5530(4) | 62(1) |
| C(26) | −2061(6) | 6176(2) | 4177(5) | 33(1) |
| C(27) | −3538(6) | 5940(2) | 4770(6) | 35(2) |
| C(28) | −2710(7) | 5634(2) | 5256(6) | 38(2) |
| C(29) | −1565(7) | 5637(2) | 5238(6) | 38(2) |
| C(30) | 84(6) | 5918(2) | 4754(5) | 32(1) |
| C(31) | 1757(6) | 5545(2) | 4799(6) | 34(2) |
| C(32) | 2320(6) | 5811(2) | 5667(5) | 34(2) |
| C(33) | 1125(7) | 6014(2) | 5697(6) | 38(2) |
| C(34) | 2224(7) | 5144(2) | 4906(6) | 35(2) |
| C(35) | 882(8) | 4453(2) | 6664(7) | 50(2) |
| C(36) | 404(11) | 4719(4) | 7049(10) | 78(3) |
| C(37) | −867(11) | 4722(4) | 6911(10) | 88(4) |
| C(38) | −1658(11) | 4449(4) | 6353(11) | 91(4) |
| C(39) | −1148(11) | 4166(4) | 5937(10) | 84(4) |
| C(40) | 101(10) | 4166(3) | 6074(9) | 69(3) |
| C(41) | 4806(7) | 4794(2) | 7341(6) | 43(2) |
| C(42) | 6103(8) | 4628(3) | 7868(6) | 59(2) |
| C(43) | 4987(7) | 5214(3) | 7111(7) | 48(2) |
| C(44) | 5647(11) | 5817(3) | 7891(9) | 71(3) |
| C(45) | 7060(10) | 5779(2) | 8217(8) | 60(2) |
| C(46) | 7713(12) | 5808(4) | 7623(9) | 79(3) |
| C(47) | 8991(14) | 5754(5) | 7926(10) | 98(4) |
| C(48) | 9642(12) | 5675(4) | 8866(10) | 82(3) |
| C(49) | 9007(11) | 5644(3) | 9451(9) | 74(3) |
| C(50) | 7752(11) | 5689(3) | 9171(8) | 67(3) |
| N(5) | −1179(5) | 5908(2) | 4744(5) | 34(1) |
| N(6) | −3210(5) | 6187(2) | 4213(5) | 35(1) |
| N(7) | −4662(6) | 5986(2) | 4836(5) | 43(2) |
| N(8) | 4572(2) | 4572(2) | 6488(5) | 41(1) |
| O(9) | −1723(5) | 6398(1) | 3670(4) | 40(1) |
| O(10) | 423(4) | 5538(1) | 4567(4) | 36(1) |
| O(11) | 3246(5) | 6065(2) | 5588(4) | 41(1) |
| O(12) | 2070(5) | 4969(1) | 5727(4) | 37(1) |
| O(13) | 2175(5) | 4448(2) | 6814(4) | 43(1) |
| O(14) | 2253(5) | 4294(1) | 5142(4) | 41(1) |
| O(15) | 5126(5) | 5327(2) | 6402(4) | 47(1) |
| O(16) | 5079(6) | 5439(2) | 7854(5) | 59(2) |
| P(2) | 2638(2) | 4552(1) | 5976(1) | 36(1) |
| F(3) | 848(4) | 5870(2) | 6437(3) | 53(1) |
| F(4) | 1260(4) | 6399(1) | 5827(4) | 52(1) |
| C(51) | 1164(6) | 6520(2) | 10539(5) | 33(2) |
| C(52) | −905(6) | 6744(2) | 9936(6) | 35(2) |
| C(53) | −566(7) | 7031(2) | 9380(6) | 40(2) |
| C(54) | 599(7) | 7038(2) | 9410(6) | 36(2) |
| C(55) | 2751(6) | 6779(2) | 9946(5) | 32(1) |
| C(56) | 4386(6) | 7140(2) | 9914(5) | 32(1) |
| C(57) | 4124(6) | 6867(2) | 9056(5) | 34(2) |
| C(58) | 2905(7) | 6665(2) | 9004(5) | 34(2) |
| C(59) | 4765(6) | 7544(2) | 9783(6) | 35(2) |
| C(60) | 1742(7) | 8055(2) | 7650(7) | 47(2) |
| C(61) | 1252(10) | 7835(3) | 6826(8) | 68(3) |
| C(62) | 84(11) | 7676(4) | 6616(10) | 82(3) |
| C(63) | −591(8) | 7726(3) | 7205(9) | 64(3) |
| C(64) | −89(8) | 7946(2) | 7989(8) | 54(2) |
| C(65) | 1092(8) | 8113(2) | 8209(7) | 52(2) |
| C(66) | 5145(7) | 7905(2) | 7409(6) | 41(2) |
| C(67) | 6043(9) | 8071(3) | 6954(7) | 53(2) |
| C(68) | 5468(8) | 7483(2) | 7619(6) | 42(2) |
| C(69) | 5155(10) | 6864(3) | 6889(8) | 60(2) |
| C(70) | 6264(9) | 6846(2) | 6585(7) | 53(2) |
| C(71) | 6155(10) | 6982(3) | 5686(8) | 59(2) |
| C(72) | 7172(12) | 6977(3) | 5408(9) | 71(3) |
| C(73) | 8315(12) | 6830(3) | 5991(10) | 75(3) |
| C(74) | 8438(12) | 6699(4) | 6868(10) | 81(3) |
| C(75) | 7418(11) | 6703(3) | 7169(8) | 67(3) |
| N(9) | 1491(5) | 6777(2) | 9943(5) | 34(1) |
| N(10) | −10(5) | 6508(2) | 10508(5) | 35(1) |
| N(11) | −2054(6) | 6705(2) | 9902(5) | 41(2) |
| N(12) | 5259(6) | 8126(2) | 8254(5) | 41(1) |
| O(17) | 2023(4) | 6309(1) | 11077(4) | 39(1) |
| O(18) | 3243(4) | 7154(1) | 10110(4) | 35(1) |
| O(19) | 5136(5) | 6622(1) | 9151(4) | 39(1) |
| O(20) | 3850(4) | 7708(2) | 8941(4) | 37(1) |
| O(21) | 2929(5) | 8222(2) | 7826(4) | 46(2) |
| O(22) | 4481(5) | 8389(1) | 9527(4) | 41(1) |
| O(23) | 6271(6) | 7362(2) | 8322(4) | 49(1) |
| O(24) | 4745(5) | 7264(2) | 6883(5) | 53(2) |
| P(3) | 4158(2) | 8129(1) | 8706(1) | 36(1) |
| F(5) | 1915(4) | 6800(2) | 8253(3) | 50(1) |
| F(6) | 2937(5) | 6285(1) | 8908(4) | 53(1) |
| C(76) | 3540(7) | 11117(2) | 8649(6) | 35(2) |
| C(77) | 1484(7) | 10884(2) | 8173(6) | 39(2) |
| C(78) | 1778(7) | 10570(2) | 7671(6) | 40(2) |
| C(79) | 2942(7) | 10551(2) | 7677(5) | 35(2) |
| C(80) | 5100(7) | 10796(2) | 8131(5) | 35(2) |
| C(81) | 6303(6) | 10530(2) | 7384(6) | 35(2) |
| C(82) | 6961(7) | 10396(2) | 8421(6) | 40(2) |
| C(83) | 6006(7) | 10527(2) | 8865(6) | 41(2) |
| C(84) | 6246(7) | 10233(2) | 6633(6) | 39(2) |
| C(85) | 3528(7) | 9348(2) | 6559(6) | 38(2) |
| C(86) | 2822(8) | 9666(2) | 6114(7) | 48(2) |
| C(87) | 1628(8) | 9720(2) | 6144(7) | 48(2) |
| C(88) | 1173(9) | 9470(3) | 6643(9) | 67(3) |
| C(89) | 1910(11) | 9160(4) | 7098(11) | 94(5) |
| C(90) | 3074(10) | 9099(3) | 7046(9) | 71(3) |
| C(91) | 7615(8) | 9178(2) | 7289(7) | 49(2) |
| C(92) | 8505(9) | 8866(2) | 7193(9) | 64(3) |
| C(93) | 8450(7) | 9499(3) | 7889(6) | 47(2) |
| C(94) | 9666(9) | 9667(3) | 9478(7) | 62(3) |
| C(95) | 10946(8) | 9549(3) | 9561(6) | 50(2) |
| C(96) | 11759(10) | 9775(3) | 9326(8) | 61(2) |
| C(97) | 12923(11) | 9654(4) | 9378(10) | 84(4) |
| C(98) | 13298(11) | 9271(4) | 9690(10) | 84(4) |
| C(99) | 12498(11) | 9039(3) | 9906(8) | 70(3) |
| C(100) | 11361(10) | 9177(3) | 9876(8) | 63(3) |
| N(13) | 3848(5) | 10818(2) | 8143(5) | 34(1) |
| N(14) | 2369(6) | 11140(2) | 8647(5) | 38(1) |
| N(15) | 343(6) | 10931(2) | 8180(5) | 48(2) |
| N(16) | 6823(6) | 9309(2) | 6359(5) | 44(2) |
| O(25) | 4392(5) | 11344(2) | 9089(4) | 46(1) |
| O(26) | 5042(5) | 10633(1) | 7266(4) | 39(1) |
| O(27) | 8180(5) | 10544(2) | 8843(5) | 51(2) |
| O(28) | 5706(5) | 9886(1) | 6841(4) | 39(1) |
| O(29) | 4702(5) | 9262(1) | 6535(4) | 39(1) |
| O(30) | 4937(5) | 9639(1) | 5117(4) | 41(1) |
| O(31) | 8836(5) | 9768(2) | 7578(5) | 50(1) |
| O(32) | 8700(6) | 9428(2) | 8821(5) | 62(2) |
| P(4) | 5510(2) | 9535(1) | 6125(1) | 36(1) |
| F(7) | 5347(5) | 10213(1) | 8974(4) | 55(1) |
| F(8) | 6542(5) | 10684(2) | 9723(4) | 61(1) |
| C(101) | 6810(20) | 9411(8) | 10080(20) | 93(8) |
| C(102) | 6300(20) | 9155(6) | 9290(15) | 83(7) |
| N(17) | 7140(30) | 9630(9) | 10710(20) | 148(12) |

Example 2

The solubilities of NUC-1031 and its diastereoisomers were determined in a range of pharmaceutically acceptable solvent systems. The protocol adopted was as follows:

A small volume, 1-2 mL, of each solvent system was prepared and a weight of the compound in question was added. The solutions were stirred for approximately 4 hours and then 0.45 µL membrane filtered. The concentration of the compound in question in the filtrate was then determined by HPLC assay.

Based on the gemcitabine dosage schedule used in the treatment of pancreatic cancer, the molecular weight adjusted dose of NUC-1031 would be about 3200 mg, given as an infusion once weekly. As an indication of the level of solubility required, taking a notional target of a 500 mL infusion volume, the required solubility of the NUC-1031 would be >6 mg/ml in the infusion fluid. However, this solubility level is just an indication and solubilities below can still provide effective therapies.

Table 5 shows the solubility of a gemcitabine-[phenyl-benzoxy-L-alaninyl)]-phosphate 2 epimeric mixture in a range of solvents suitable for intravenous administration.

| Solvent | Appearance | Assay (mg/ml) |
|---|---|---|
| Ethanol | Solubilised quickly, after 30 minutes precipitated out to white paste | |
| Glycerol | API evident | |
| Propylene glycol | Precipitation evident after 30 minutes | 371 |
| PEG 400 | Precipitation evident after 120 minutes | 385 |
| NMP | Clear solution | >207 |
| DMSO | Clear solution | >217 |

Table 6 shows the solubility of the two gemcitabine-[phenyl-benzoxy-L-alaninyl)]-phosphate epimers 3 and 4 in a range of solvent/water mixtures.

| Solvent (percentage by volume) | Solubility (R)-epimer (mg/mL) 4 | Solubility (S)-epimer (mg/mL) 3 |
|---|---|---|
| PROPYLENE GLYCOL (10%) | 0 | 0.23 |
| PROPYLENE GLYCOL (50%) | 0.11 | 11.29 |
| PEG400 (10%) | 0 | 0.46 |
| PEG400 (50%) | 0.27 | 32.13 |
| ETHANOL (10%) | 0 | 0.27 |
| ETHANOL (50%) | 0.69 | 34.79 |

As can be seen from Table 6, the (R)-epimer 4 is substantially insoluble in 10% mixtures of polar organic solvents in water. The (S)-epimer 3, on the other hand, shows a significantly improved solubility. In 50% mixtures of polar organic solvents in water, the (S)-epimer 3 can be over 100 fold more soluble than the (R)-epimer 4. The (S)-epimer can thus provide a potentially very convenient and effective therapy.

Example 3

To evaluate the differential uptake of the (R)- and (S)-epimers into cyclodextrin, $^{31}$P NMR spectra of NUC-1031 isomers mixture after treatment with HP-β-CD in D$_2$O was recorded.

Figure 5:
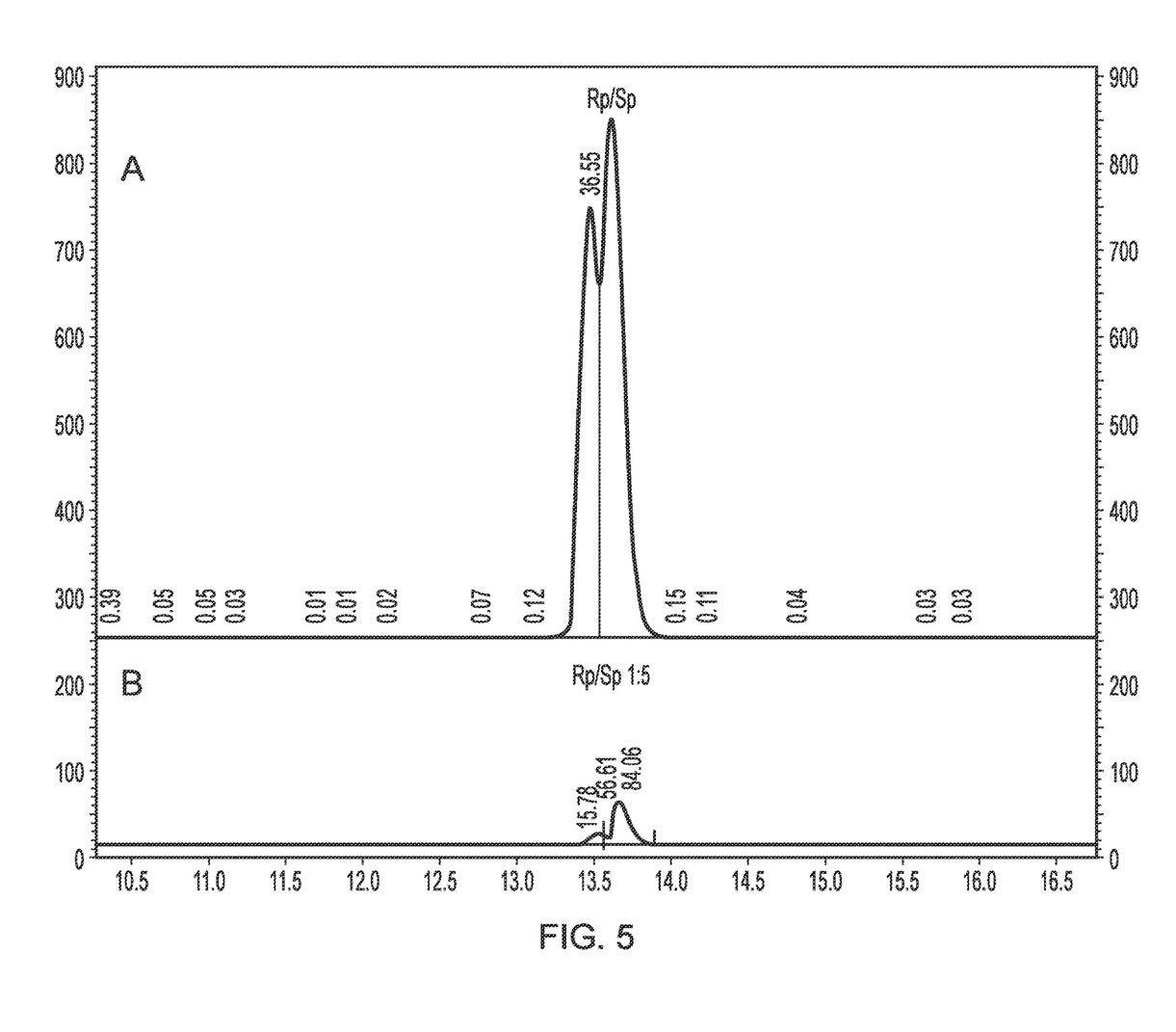
FIG. 5 shows the HPLC traces of NUC-1031 (3.12 mM) in MeOH (A) in H$_2$O after addition of HP-β-CD in a 1:2.3 molar ratio (B).

NMR studies. $^1$H NMR (500 MHz) and $^{31}$P NMR (202 MHz) were recorded on a Bruker Avance 500 MHz spectrometer at 25° C. Chemical shifts (δ) are quoted in parts per million (ppm) relative to internal D$_2$O (δ 4.9 $^1$H NMR) or external 85% H$_3$PO$_4$ (δ 0.00 $^{31}$P NMR). Both HPLC and NMR studies were carried out at room temperature HPLC studies. Analytical High Performance Liquid Chromatography (HPLC) analysis was performed using a ThermoScientific system. Reverse-phase HPLC analyses were carried out on a SCIENTIFIC Hypersil Gold C18, 5µ, 150×4.6 mm eluting with H$_2$O/CH$_3$CN from 90/10 to 0/100 in 30 min at a flow rate of 1 mL/min and at the detection wavelength of 280 nm. The retention times of NUC-1031 epimers (dissolved in MeOH) are observed respectively at 13.58 min for the (S)-epimer 3 and at 13.44 min for the (R)-epimer 4 under these conditions (FIG. 5A).

2.36 mg of NUC-1031 isomer mixture (1:1.1 (S):(R)) was weighed and transferred into a NMR tube. 13.3 mg of HP-β-CD was then dissolved in 1.3 mL of deuterium oxide and this was solution added to the NMR tube (1:2.3 molar ratio NUC1031: HP-β-CD) (NOTE: not all the solid dissolved in the solution).

Figure 4:
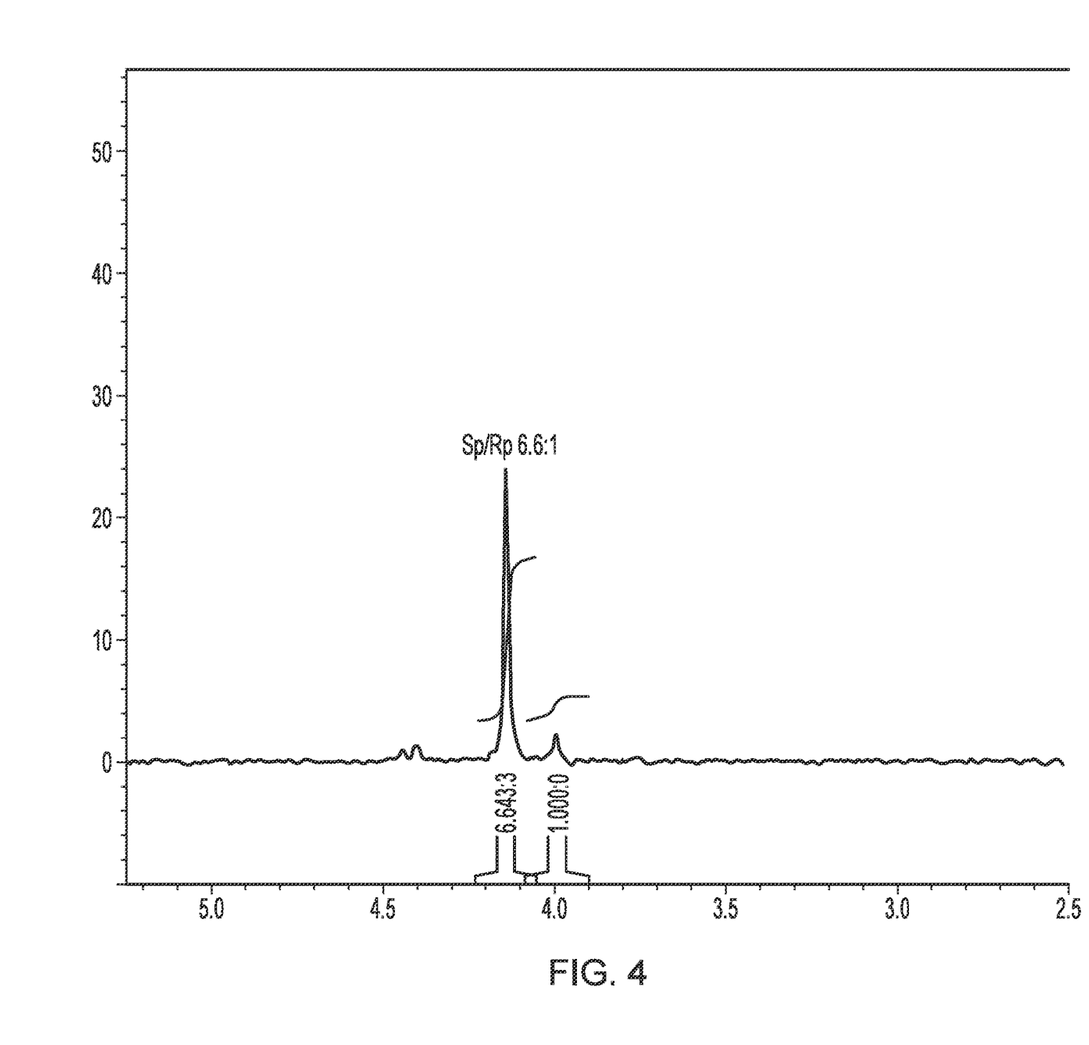
FIG. 4 shows the $^{31}$P-NMR spectrum (202 MHz, D$_2$O) of NUC-1031 isomeric mixture (3.12 mM), after addition of HP-β-CD in a 1:2.3 molar ratio.

The $^{31}$P NMR spectrum shows that HP-β-CD is able to enhance the solubility of NUC-1031 (S)-epimer 3 (4.14 Hz) relative to the (R)-epimer (4.00 Hz), with the observed ratio of (S)- and (R)-epimers in solution being 6.6:1 in favour of the (S)-epimer (FIG. 4).

0.5 mL of the D$_2$O solution from the NMR study was diluted to 1 mL by addition of 0.5 mL of water (1.15 mg/mL). 20 µL of this solution were injected into the HPLC.

HPLC analysis of the diluted NMR sample confirmed that the (S)-epimer 3 is taken up into solution better than the (R)-epimer 4, with the observed ratio of (S)- and (R)-epimers in solution being 5:1 in favour of the (S)-epimer, broadly in agreement with the NMR data (FIG. 5B).

Similar studies conducted with another gemcitabine phosphate derivative showed no difference between the uptake of the (S)- and (R)-epimers of that derivative into a cyclodextrin solution.

Example 4

The clearance and bioavailability of most medicines are strongly influenced by their first-pass metabolism in the liver. It is possible to estimate the relative hepatic "metabolic stability" in vitro by incubating compounds with cryopreserved hepatocytes and determining the initial vs. the final amount of the test compound in the incubation mixtures.

The following procedure is an HPLC-MS/MS assay using pooled human cryopreserved hepatocyte suspension.

Assay Matrix

Human hepatocytes: mixed gender and pool of 10

Final cell density: 1 million (10$^6$) viable cells/mL

Experimental Protocol

Pooled cryopreserved hepatocytes are thawed, washed, and resuspended in Krebs-Heinslet buffer (pH 7.3). The reaction is initiated by adding the test compound (1 µM final concentration) into cell suspension and incubated in a final volume of 100 µL on a flat-bottom 96-well plate for 0 minute and 120 minutes, respectively, at 37° C./5% CO$_2$. The reaction is stopped by adding 100 µL of acetonitrile into the incubation mixture. Samples are then mixed gently and briefly on a plate shaker, transferred completely to a 0.8 mL V-bottom 96-well plate, and centrifuged at 2550× g for 15 minutes at room temperature. Each supernatant (150 µL) is transferred to a clean cluster tube, followed by HPLC-MS/MS analysis on a Thermo Electron triple-quadrupole system.

This assay was modified for half-life determination. In this case, the sampling time points are 0, 30, 60, 90, and 120 minutes.
Reference Compounds Four reference compounds (1 µM) were tested simultaneously with the test compounds. Propranolol is relatively stable with human hepatocytes, whereas flurazepam, naloxone, and terfenadine are relatively unstable with human hepatocytes.
Analytical Methods Samples are analyzed via (RP)HPLC-MS/MS using selected reaction monitoring (SRM). The HPLC conditions consist of an HP1100 binary pump with autosampler, a C-12 mixed-mode, 2×20 mm column, and a gradient.
Data Analysis Peak areas corresponding to the test compound are recorded by HPLC-MS/MS. The metabolic stability, expressed as percent of the test compound remaining, is calculated by comparing the peak areas of the test compound at 2 hours to time zero. In case of half-life determination, the half-life is estimated from the slope of the initial linear range of the logarithmic curve of the test compound remaining (%) vs. time, assuming first order kinetics.

The results are shown in Table 7.

Table 7 shows intrinsic clearances of the S epimer, the R epimer and a mixture of the two epimers 3 or a pharmaceutically acceptable salt or solvate thereof, and a further component, wherein said further component is selected from a polar organic solvent, a cyclodextrin, and both a polar organic solvent and a cyclodextrin; wherein the gemcitabine-[phenyl-(benzoxy-L-alaninyl)]-(S)- phosphate 3 has a diastereoisomeric purity of greater than about 90%, and the pharmaceutical solution is for intravenous administration.

2. The pharmaceutical solution of claim 1, wherein the solution comprises the polar organic solvent.

3. The pharmaceutical solution of claim 2, wherein the polar organic solvent is selected from the group consisting of propylene glycol, polyethylene glycol and ethanol.

4. The pharmaceutical solution of claim 3, wherein the polar organic solvent is propylene glycol.

5. The pharmaceutical solution of claim 3, wherein the polar organic solvent is polyethylene glycol.

6. The pharmaceutical solution of claim 5, wherein the polyethylene glycol is PEG400.

7. The pharmaceutical solution of claim 3, wherein the polar organic solvent is ethanol.

|  | Test Concentration (M) | Incubation Time (minutes) | % Compound Remaining | | | | Half-Life (minute) | | | | Clint |
|---|---|---|---|---|---|---|---|---|---|---|---|
|  |  |  | 1st | 2nd | 3rd | Mean | 1st | 2nd | 3rd | Mean |  |
| R/S Mix | 1.0E−06 | 0 | 100.0 | 100.0 | 100.0 | 100.0 | 72.9 | 72.5 | 82.2 | 76 | 13.10 |
|  | 1.0E−06 | 30 | 64.3 | 68.7 | 74.3 | 69.1 |  |  |  |  | 13.10 |
|  | 1.0E−06 | 60 | 56.5 | 56.3 | 60.3 | 57.7 |  |  |  |  | 13.10 |
|  | 1.0E−06 | 90 | 59.6 | 55.9 | 45.2 | 53.6 |  |  |  |  | 13.10 |
|  | 1.0E−06 | 120 | 36.9 | 56.8 | 53.9 | 49.2 |  |  |  |  | 13.10 |
| S | 1.0E−06 | 0 | 100.0 | 100.0 | 100.0 | 100.0 | 40.5 | 36.5 | 35.0 | 37 | 26.60 |
|  | 1.0E−06 | 30 | 47.2 | 57.6 | 52.9 | 52.6 |  |  |  |  | 26.60 |
|  | 1.0E−06 | 60 | 35.8 | 32.0 | 30.4 | 32.7 |  |  |  |  | 26.60 |
|  | 1.0E−06 | 90 | 25.0 | 26.0 | 30.2 | 27.0 |  |  |  |  | 26.60 |
|  | 1.0E−06 | 120 | 31.0 | 30.6 | 35.6 | 32.4 |  |  |  |  | 26.60 |
| R | 1.0E−06 | 0 | 100.0 | 100.0 | 100.0 | 100.0 | 471.6 | >120 | >120 | >120 | <8.2 |
|  | 1.0E−06 | 30 | 80.2 | 86.9 | 94.3 | 87.1 |  |  |  |  | <8.2 |
|  | 1.0E−06 | 60 | 97.4 | {2.1} | {1.3} | 97.4 |  |  |  |  | <8.2 |
|  | 1.0E−06 | 90 | 73.6 | 91.6 | 88.0 | 84.4 |  |  |  |  | <8.2 |
|  | 1.0E−06 | 120 | 83.8 | 108.5 | 111.4 | 101.2 |  |  |  |  | <8.2 |

The invention claimed is:

1. A pharmaceutical solution formulation, comprising water, gemcitabine[phenyl-(benzoxy-L-alaninyl)]-(S)-phosphate 3:

8. The pharmaceutical solution of claim 1, wherein the solution comprises the cyclodextrin.

9. The pharmaceutical solution of claim 8, wherein the cyclodextrin is selected from the group consisting of a-cyclodextrin, (3-cyclodextrin, y-cyclodextrin, 2-hydroxypropyl-P-cyclodextrin, sulfobutylether (3-cyclodextrin sodium salt, and partially methylated 3-cyclodextrin.

10. The pharmaceutical solution of claim 1, wherein the gemcitabine-[phenyl-(benzoxy-L-alaninyl)]-(S)-phosphate 3 is in the form of a free base.

11. The pharmaceutical solution of claim 1, wherein gemcitabine-[phenyl-(benzoxy-L-alaninyl)]-(5)-phosphate 3 has a diastereoisomeric purity of greater than about 95%.

12. The pharmaceutical solution of claim 1, wherein gemcitabine-[phenyl-(benzoxy-L-alaninyl)]-(5)-phosphate 3 has a diastereoisomeric purity of greater than about 98%.

13. The pharmaceutical solution of claim 1, wherein gemcitabine-[phenyl-(benzoxy-L-alaninyl)]-(5)-phosphate 3 has a diastereoisomeric purity of greater than about 99.5%.

* * * * *